US006562945B1

(12) United States Patent
Shi-Hsiang et al.

(10) Patent No.: US 6,562,945 B1
(45) Date of Patent: May 13, 2003

(54) GALANIN RECEPTOR

(75) Inventors: Shen Shi-Hsiang, Beaconsfield (CA); Ahmad Sultan, Dorval (CA); Claes Wahlestedt, Montreal (CA); Philippe Walker, Montreal (CA)

(73) Assignee: AstraZeneca Canada Inc., Mississauga (CA)

( * ) Notice: Subject to any disclaimer, the term of this patent is extended or adjusted under 35 U.S.C. 154(b) by 474 days.

(21) Appl. No.: 08/981,700

(22) PCT Filed: Jul. 4, 1997

(86) PCT No.: PCT/SE97/01217

§ 371 (c)(1),
(2), (4) Date: Jan. 9, 1998

(87) PCT Pub. No.: WO98/03548

PCT Pub. Date: Jan. 29, 1998

(30) Foreign Application Priority Data

Jul. 19, 1996 (SE) .......................................... 9602822-0

(51) Int. Cl.[7] ...................... C07K 14/705; C12N 15/09; C12N 15/70; C12N 5/06

(52) U.S. Cl. .................. 530/350; 435/69.1; 435/320.1; 435/325

(58) Field of Search ......................... 530/350; 435/69.1, 435/320.1, 325

(56) References Cited

U.S. PATENT DOCUMENTS 5,972,624 A 10/1999 Smith et al.

FOREIGN PATENT DOCUMENTS

| | | | |
|---|---|---|---|
| EP | 711 830 | 5/1996 | ........... C12N/15/12 |
| WO | WO 92/15015 | 9/1992 | .......... G01N/33/68 |
| WO | WO 95/22608 | 8/1995 | ........... C12N/15/12 |
| WO | WO 97/26853 | 7/1997 | |
| WO | WO 98/29439 | 7/1998 | ........... C07K/14/00 |
| WO | WO 98/29440 | 7/1998 | ........... C07K/14/00 |
| WO | WO 98/29441 | 7/1998 | ........... C07K/14/00 |

OTHER PUBLICATIONS

Dialog abstract of French counterpart of WO 95/22608 (listed above as document AN1), Derwent World Patents Index accession No. 95–285172/199538.

International Search Report for Swedish appl. 9602822–0(priority appl. of PCT/SE97/01217).

*Primary Examiner*—Gary Kunz
*Assistant Examiner*—Stephen Gucker
(74) *Attorney, Agent, or Firm*—Michael A. Sanzo; Fitch, Even, Tabin & Flannery

(57) ABSTRACT

The present invention is directed to a novel receptor for galanin which has been designated as galanin receptor 2. The invention encompasses both the receptor protein as well as nucleic acids encoding the protein. In addition, the present invention is directed to methods and compositions which rely upon either GAL-R2 proteins or nucleic acids.

8 Claims, 11 Drawing Sheets

```
                         25                        50                        75                       100
                          *                         *                         *                         *
CCGCGCGCACACCGCTCCCTCCACA CCTCCAGGGGGAGTGAGCCACTCAA GTCTAAAGCAGAGCGAGTCCCAGGA CTTGAGCGCGGGAAGCGAATGGAGT

                        125                       150                       175                       200
                          *                         *                         *                         *
CAGGGTCATTCGATTGCACCTCTCT CGACTGCGGGCCGGAGCGGGGTACC ATCCTACACTCTGGGTGCTCCCTCC TCCTCCCGTCCCCCGCGCACCCCTC

                        225                       250                       275                       300
                          *                         *                         *                         *
CCCTGTCTCCTGGAGCTCGGCAGTC TCGCTGGGGCGCTGCAGCGAGGGAG CAGCGTGCTCACCAAGGACCCGGAC AGCTGCGGGAGCGGCGTCCACTTTG

                  325                             350                             375
                    *                               *                               *
GTGATACC ATG AAT GGC TCC GGC AGC CAG GGC GCG GAG AAC ACG AGC CAG GAA GGC AGT AGC GGC GGC TGG CAG CCT GAG
          M   N   G   S   G   S   Q   G   A   E   N   T   S   Q   E   G   S   S   G   G   W   Q   P   E

              400                             425                             450
                *                               *                               *
GCG GTC CTT GTA CCC CTA TTT TTC GCG CTC ATC TTC CTC GTG GGC ACC GTG GGC AAC GCG CTG GTG CTG GCG GTG CTG
 A   V   L   V   P   L   F   F   A   L   I   F   L   V   G   T   V   G   N   A   L   V   L   A   V   L

          475                             500                             525
            *                               *                               *
CTG CGC GGC GGC CAG GCG GTC AGC ACC ACC AAC CTG TTC ATC CTC AAC CTG GGC GTG GCC GAC CTG TGT TTC ATC CTG
 L   R   G   G   Q   A   V   S   T   T   N   L   F   I   L   N   L   G   V   A   D   L   C   F   I   L
```

FIG.1A

```
                      550                                                  575                                                   600
                       *                                                    *                                                     *
TGC TGC GTG CCT TTC CAG GCC ACC ATC TAC ACC CTG GAC GAC TGG GTG TTC GGC TCG CTG CTC TGC AAG GCT GTT CAT
 C   C   V   P   F   Q   A   T   I   Y   T   L   D   D   W   V   F   G   S   L   L   C   K   A   V   H

              625                                                 650                                                   675
               *                                                   *                                                     *
TTC CTC ATC TTT CTC ACT ATG CAC GCC AGC AGC TTC ACG CTG GCC GCC GTC TCC CTG GAC AGG TAT CTG GCC ATC CGC
 F   L   I   F   L   T   M   H   A   S   S   F   T   L   A   A   V   S   L   D   R   Y   L   A   I   R

          700                                                 725                                                 750
           *                                                   *                                                   *
TAC CCG CTG CAC TCC CGA GAG TTG CGC ACA CCT CGA AAC GCG CTG GCC GCC ATC GGG CTC ATC TGG GGG CTA GCA CTG
 Y   P   L   H   S   R   E   L   R   T   P   R   N   A   L   A   A   I   G   L   I   W   G   L   A   L

      775                                                 800                                                 825
       *                                                   *                                                   *
CTC TTC TCC GGG CCC TAC CTG AGC TAC TAC CGT CAG TCG CAG CTG GCC AAC CTG ACA GTA TGC CAC CCA GCA TGG AGC
 L   F   S   G   P   Y   L   S   Y   Y   R   Q   S   Q   L   A   N   L   T   V   C   H   P   A   W   S

850                                                 875                                                 900                                                 925
 *                                                   *                                                   *                                                   *
GCA CCT CGA CGT CGA GCC ATG GAC CTC TGC ACC TTC GTC TTT AGC TAC CTG CTG CCA GTG CTA GTC CTC AGT CTG ACC
 A   P   R   R   R   A   M   D   L   C   T   F   V   F   S   Y   L   L   P   V   L   V   L   S   L   T
```

FIG.1B

```
                                          950                                            975                                        1000
                                           *                                              *                                           *
TAT GCG CGT ACC CTG CGC TAC CTC TGG CGC ACA GTC GAC CCG GTG ACT GCA GGC TCA GGT TCC CAG CGC GCC AAA CGC
 Y   A   R   T   L   R   Y   L   W   R   T   V   D   P   V   T   A   G   S   G   S   Q   R   A   K   R

                                     1025                                       1050                                        1075
                                       *                                          *                                           *
AAG GTG ACA CGG ATG ATC ATC ATC GTG GCG GTG CTT TTC TGC CTC TGT TGG ATG CCC CAC CAC GCG CTT ATC CTC TGC
 K   V   T   R   M   I   I   I   V   A   V   L   F   C   L   C   W   M   P   H   H   A   L   I   L   C

                           1100                                        1125                                       1150
                             *                                           *                                          *
GTG TGG TTT GGT CGC TTC CCG CTC ACG CGT GCC ACT TAC GCG TTG CGC ATC CTT TCA CAC CTA GTT TCC TAT GCC AAC
 V   W   F   G   R   F   P   L   T   R   A   T   Y   A   L   R   I   L   S   H   L   V   S   Y   A   N

                      1175                                        1200                                        1225
                        *                                           *                                           *
TCC TGT GTC AAC CCC ATC GTT TAC GCT CTG GTC TCC AAG CAT TTC CGT AAA GGT TTC CGC AAA ATC TGC GCG GGC CTG
 S   C   V   N   P   I   V   Y   A   L   V   S   K   H   F   R   K   G   F   R   K   I   C   A   G   L

           1250                                        1275                                       1300
             *                                           *                                          *
CTG CGC CCT GCC CCG AGG CGA GCT TCG GGC CGA GTG AGC ATC CTG GCG CCT GGG AAC CAT AGT GGC AGC ATG CTG GAA
 L   R   P   A   P   R   R   A   S   G   R   V   S   I   L   A   P   G   N   H   S   G   S   M   L   E
```

FIG.1C

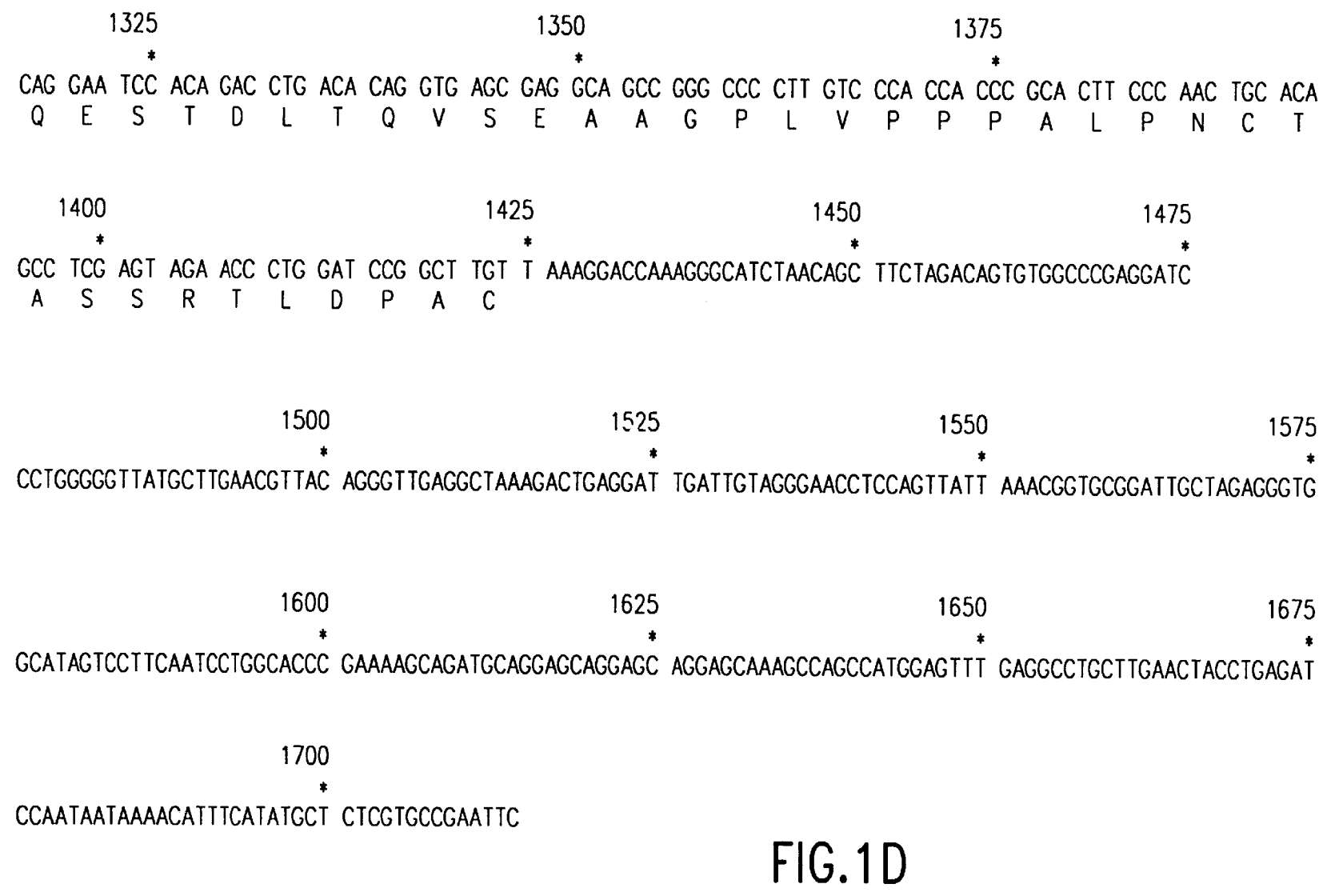

```
1325                       1350                         1375
   *                          *                            *
CAG GAA TCC ACA GAC CTG ACA CAG GTG AGC GAG GCA GCC GGG CCC CTT GTC CCA CCA CCC GCA CTT CCC AAC TGC ACA
 Q   E   S   T   D   L   T   Q   V   S   E   A   A   G   P   L   V   P   P   P   A   L   P   N   C   T

1400                      1425                      1450                      1475
   *                         *                         *                         *
GCC TCG AGT AGA ACC CTG GAT CCG GCT TGT T AAAGGACCAAAGGGCATCTAACAGC TTCTAGACAGTGTGGCCCGAGGATC
 A   S   S   R   T   L   D   P   A   C

                     1500                      1525                      1550                      1575
                        *                         *                         *                         *
CCTGGGGGTTATGCTTGAACGTTAC AGGGTTGAGGCTAAAGACTGAGGAT TGATTGTAGGGAACCTCCAGTTATT AAACGGTGCGGATTGCTAGAGGGTG

                     1600                      1625                      1650                      1675
                        *                         *                         *                         *
GCATAGTCCTTCAATCCTGGCACCC GAAAAGCAGATGCAGGAGCAGGAGC AGGAGCAAAGCCAGCCATGGAGTTT GAGGCCTGCTTGAACTACCTGAGAT

                     1700
                        *
CCAATAATAAAACATTTCATATGCT CTCGTGCCGAATTC
```

FIG.1D

```
                              30                                      60                                      90
            *           *           *           *           *           *           *           *           *           *           *
GGGTCAGCGGCACC ATG AAC GTC TCG GGC TGC CCA GGG GCC GGG AAC GCG AGC CAG GCG GGC GGC GGG GGA GGC TGG CAC CCC GAG GCG GTC ATC GTG CCC CTG CTC TTC GCG
                M   N   V   S   G   C   P   G   A   G   N   A   S   Q   A   G   G   G   G   W   H   P   E   A   V   I   V   P   L   L   F   A

    120                                     150                                     180                                     210
     *           *           *           *           *           *           *           *           *           *           *
CTC ATC TTC CTC GTG GGC ACC GTG GGC AAC ACG CTG GTG CTG GCG GTG CTG CTG CGC GGC GGC CAG GCG GTC AGC ACT ACC AAC CTG TTC ATC CTT AAC CTG GGC GTG GCC
 L   I   F   L   V   G   T   V   G   N   T   L   V   L   A   V   L   L   R   G   G   Q   A   V   S   T   T   N   L   F   I   L   N   L   G   V   A

                240                                     270                                     300                                     330
 *           *           *           *           *           *           *           *           *           *           *
GAC CTG TGT TTC ATC CTG TGC TGC GTG CCC TTC CAG GCC ACC ATC TAC ACC CTG GAC GGC TGG GTG TCC GGC TCG CTG CTG TGC AAG GCG GTG CAC TTC CTC ATC TTC CTC
 D   L   C   F   I   L   C   C   V   P   F   Q   A   T   I   Y   T   L   D   G   W   V   F   G   S   L   L   C   K   A   V   H   F   L   I   F   L

                            360                                     390                                     420
 *           *           *           *           *           *           *           *           *           *           *
ACC ATG CAC GCC AGC AGC TTC ACG CTG GCC GCC GTC TCC CTG GAC AGG TAT TTG GCC ATC CGC TAC CCG CTG CAC TCC CGC GAG CTG CGC ACG CCT CGA AAC GCG CTG GCA
 T   M   H   A   S   S   F   T   L   A   A   V   S   L   D   R   Y   L   A   I   R   Y   P   L   H   S   R   E   L   R   T   P   R   N   A   L   A
```

FIG.2A

```
450                                     480                                     510                                     540
 *            *            *            *            *            *            *            *            *            *            *            *
GCC ATC GGG CTC ATC TGG GGG CTG TCG CTG CTC TTC TCC GGG CCC TAC CTG AGC TAC TAC CGC CAG TCG CAG CTG GCC AAC CTG ACC GTG TGC CAT CCC GCG TGG AGC GCC
 A   I   G   L   I   W   G   L   S   L   L   F   S   G   P   Y   L   S   Y   Y   R   Q   S   Q   L   A   N   L   T   V   C   H   P   A   W   S   A

                570                                     600                                     630                                     660
 *            *            *            *            *            *            *            *            *            *            *            *
CCT CGC CGC CGC GCC ATG GAC ATC TGC ACC TTC GTC TTC AGC TAC CTG CTT CCT GTG CTG GTT CTG GGC CTG ACC TAC GCG CGC ACC TTG CGC TAC CTC TGG CGC GCC GTC
 P   R   R   R   A   M   D   I   C   T   F   V   F   S   Y   L   L   P   V   L   V   L   G   L   T   Y   A   R   T   L   R   Y   L   W   R   A   V

                            690                                     720                                     750
 *            *            *            *            *            *            *            *            *            *            *            *
GAC CCG GTG GCC GCG GGC TCG GGT GCC CGG CGC GCC AAG CGC AAG GTG ACA CGC ATG ATC CTC ATC GTG GCC GCG CTC TTC TGC CTC TGC TGG ATG CCC CAC CAC GCG CTC
 D   P   V   A   A   G   S   G   A   R   R   A   K   R   K   V   T   R   M   I   L   I   V   A   A   L   F   C   L   C   W   M   P   H   H   A   L
```

FIG.2B

```
780                                     810                                         840                                         870
*              *             *              *              *              *              *              *              *              *              *              *
ATC CTC TGC GTG TGG TTC GGC CAG TTC CCG CTC ACG CGC GCC ACT TAT GCG CTT CGC ATC CTC TCG CAC CTG GTC TCC TAC GCC AAC TCC TGC GTC AAC CCC ATC GTT TAC
 I   L   C   V   W   F   G   Q   F   P   L   T   R   A   T   Y   A   L   R   I   L   S   H   L   V   S   Y   A   N   S   C   V   N   P   I   V   Y

          900                                         930                                         960                                         990
           *              *              *              *              *              *              *              *              *              *              *
GCG CTG GTC TCC AAG CAC TTC CGC AAA GGC TTC CGC ACG ATC TGC GCG GGC CTG CTG GGC CGT GCC CCA GGC CGA GCC TCG GGC CGT GTG TGC GCT GCC GCG CGG GGC ACC
 A   L   V   S   K   H   F   R   K   G   F   R   T   I   C   A   G   L   L   G   R   A   P   G   R   A   S   G   R   V   C   A   A   A   R   G   T

      1020                                                    1050                                         1080                                        1110
       *              *              *              *              *              *              *              *              *              *              *
CAC AGT GGC AGC GTG TTG GAG CGC GAG TCC AGC GAC CTG TTG CAC ATG AGC GAG GCG GCG GGG GCC CTT CGT CCC TGC CCC GGC GCT TCC CAG CCA TGC ATC CTC GAG CCC
 H   S   G   S   V   L   E   R   E   S   S   D   L   L   H   M   S   E   A   A   G   A   L   R   P   C   P   G   A   S   Q   P   C   I   L   E   P

                                   1140                                        1170                             1200
       *              *              *              *              *              *              *         *          *          *
TGT CCT GGC CCG TCC TGG CAG GGC CCA AAG GCA GGG CAG ACA GGC ATT CCT GAC GGT TGATGTGGCCT TGAAAGGCACTTAGCGGGCG CCTGGGATGTACAGAGTTG
 C   P   G   P   S   W   Q   G   P   K   A   G   Q   T   G   I   P   D   G
```

FIG.2C

```
1   MNVSGCPGAGNANQAGGGGGWHPEAV---------IVPLLFALIFLVGTVG HGALR2.PRO
1   MNGSGSQGAENTSQEGSSGGWQPEAV---------LVPLFFALIFLVGTVG RGALR2.PRO
1   MELAPVNLSEGNGSDPEPPA-EPRPLFGIGVENFITLVVFGLIFAMGVLG rGALR1.pro
1   MELAVGNLSEGNASCPEPPAPEPGPLFGIGVENFVTLVVFGLIFALGVLG hGALR1.pro

43  NTLVLAVLLRG--GQAVSTTNLFILNLGVADLCFILCCVPFQATIYTLDG HGALR2.PRO
43  NALVLAVLLRG--GQAVSTTNLFILNLGVADLCFILCCVPFQATIYTLDD RGALR2.PRO
50  NSLVITVLARSKPGKPRSTTNLFILNLSIADLAYLLFCIPFQATVYALPT rGALR1.pro
51  NSLVITVLARSKPGKPRSTTNLFILNLSIADLAYLLFCIPFQATVYALPT hGALR1.pro

91  WVFGSLLCKAVHFLIFLTMHASSFTLAAVSLDRYLAIRYPLHSRELRTPR HGALR2.PRO
91  WVFGSLLCKAVHFLIFLTMHASSFTLAAVSLDRYLAIRYPLHSRELRTPR RGALR2.PRO
100 WVLGAFICKFIHYFFTVSMLVSIFTLAAMSVDRYVAIVHSRRSSSLRVSR rGALR1.pro
101 WVLGAFICKFIHYFFTVSMLVSIFTLAAMSVDRYVAIVHSRRSSSLRVSR hGALR1.pro

141 NALAAIGLIWGLSLLFSGPYLSYYR---QSQLANLTVCHPAWSAPR-RRA HGALR2.PRO
141 NALAAIGLIWGLALLFSGPYLSYYR---QSQLANLTVCHPAWSAPR-RRA RGALR2.PRO
150 NALLGVGFIWALSIAMASP-VAYYQRLFH-RDSNQTFCWEHWPNQLHKKA rGALR1.pro
151 NALLGVGCIWALSIAMASP-VAYHQGLFHPRASNQTFCWEQWPDPRHKKA hGALR1.pro
```

FIG. 3A

```
              190       200       210       220       230
187 MDICTFVFSYLLPVLVLGLTYARTLRYLWRAVNPVAAGSGARRAKRKVTR HGALR2.PRO
187 MDLCTFVFSYLLPVLVLSLTYARTLRYLWRTVDPVTAGSGSQRAKRKVTR RGALR2.PRO
198 YVVCTFVFGYLLPLLLICFCYAKVLNHLHKKLKNMSKKSEA--SKKKTAQ rGALR1.pro
200 YVVCTFVFGYLLPLLLICFCYAKVLNHLHKKLKNMSKKSEA--SKKKTAQ hGALR1.pro

              240       250       260       270       280
237 MILIVAALFCLCWMPHHALILCVW--FGQFPLTRATYALRILSHLVSYAN HGALR2.PRO
237 MITIVAVLFCLCWMPHHALILCVW--FGRFPLTRATYALRILSHLVSYAN RGALR2.PRO
246 TVLVVVVVFGISWLPHH--VIHLWAEFGAFPLTPASFFFRITAHCLAYSN rGALR1.pro
248 TVLVVVVVFGISWLPHH--IIHLWAEFGVFPLTPASFLFRITAHCLAYSN hGALR1.pro

              290       300       310       320       330
285 SCVNPIVYALVSKHFRKGFRTI--CAGLLGRAPGRASGRVCAAARGTHSG HGALR2.PRO
285 SCVNPIVYALVSKHFRKGFRKI--CAGLLRPAPRRASGRVSTLAPGNHSG RGALR2.PRO
294 SSVNPIIYAFLSENFRKAYKQVFKC-------------RVC--------- rGALR1.pro
296 SSVNPIIYAFLSENFRKAYKQVFKC-------------HIR--------- hGALR1.pro

              340       350       360       370       380
333 SVLERESSDLLHMSEAAGALRPCPGASQPCILEPCPGPSWQGPKAGQTGT HGALR2.PRO
333 SMLEQESTDLTQVSEAAGPLVPPPA------LPNCTASSR-------TLD RGALR2.PRO
322 -----NESPHGDAKE-KNRIDTPPSTN-------CT-------------- rGALR1.pro
324 -----KDSHLSDTKENKSRIDTPPSTN-------CT-------------- hGALR1.pro

383 PDG                                                HGALR2.PRO
370 PAC                                                RGALR2.PRO
345 HV.                                                rGALR1.pro
348 HV.                                                hGALR1.pro
```

FIG. 3B

GALANIN RECEPTOR

CROSS REFERENCE TO RELATED APPLICATIONS

The present application represents national phase of PCT/SE97/01217, filed Jul. 4, 1997. The international application claims priority to Swedish application 9602822-0 filed on Jul. 19, 1996.

FIELD OF THE INVENTION

The present invention is in the general field of biological receptors and the various uses that can be made of such receptors. More specifically, the invention relates to nucleic acids encoding a novel galanin receptor and the receptor protein itself.

BACKGROUND AND PRIOR ART

Galanin is a small (29–30 amino acid) neuroendocrine peptide which does not belong to any known peptide family (Bedecs et al., *Int. J. Biochem. Cell. Biol.* 27: 337–349 (1995)); It is widely distributed in the central nervous system and other tissues, and has been reported to have a large number of diverse biological and pharmacological activities. Galanin has been reported to: (a) promote growth hormone release (Bauer et al., *The Lancet* 2:192–195 (1986)); (b) inhibit glucose-induced insulin release (Ahren et al., *FEBS Lett*. 299:233–237 (1988)); (c) regulate motility in the gastrointestinal tract (Fox-Thelkeld et al., *Gastroenter-ology* 101:1471–1476 (1991)); (d) stimulate feeding behavior (Crawley et al., *J. Neurosci* 10:3695–3700 (1990)); and (e) impair cognitive function (Mastropaolo et al., *Proc. Nat'l Acad. Sci. U.S.A*. 85:9841–9845 (1988)).

Of particular pharmacological interest are galanin's analgesic effects (Post et al., *Acta Physiol. Scand*. 132:583–584 (1988)). In the spinal cord, galanin inhibits nociceptive reflexes and potentiates the analgesic effect of morphine (Wiesenfeld-Hallin et al., *Neurosci. Lett*. 105:149–154 (1989)). Target administration of galanin hyperpolarizes dorsal horn neurons and chronic administration of a galanin receptor antagonist after axotomy has been reported to markedly increase autonomy in rats (Verge et al., *Neurosci. Lett*. 149:193–197 (1993)). These observations indicate that galanin, like morphine, has strong anti-nociceptive actions in vivo. Thus, the known pharmacological effects of galanin suggest potential therapeutic applications as an anesthetic or analgesic in animals and humans.

Galanin exerts its effects by binding to membrane-bound receptors. The cDNA for one such receptor ("GAL-R1") has been cloned from both humans and rats (Habert-Ortoliet et al., *Proc. Natl. Acad. Sci. U.S.A*. 91:9780–9783 (1994); Burgevin et al., *J. Mol. Neurosci*. 6:33–41 (1995)). High levels of rat GAL-R1 mRNA have been found in the ventral hippocampus, thalamus, amygdala, and medulla oblongata of the brain and in the dorsal horn of the spinal cord (Burgevin et al., supra). Pharmacological data obtained using galanin fragments, agonists and antagonists have suggested that more than one type of receptor may be responsible for galanin's actions (for a review, see Valkna et al., *Neurosci. Lett*. 187:75–78 (1995)). The isolation and characterization of new receptors for galanin would be highly desirable to assist in the discovery and development of therapeutic agents for altering galanin activity in vivo.

SUMMARY OF THE INVENTION

The present invention is based upon the discovery of a novel galanin receptor ("GAL-R2") which is distinct from previously reported receptors in terms of structure, tissue distribution and binding characteristics. Receptors from both the rat and human have been isolated and sequenced. As used herein, the term "GAL-R2" refers to the receptor from either of these species unless the text, expressly or by context, indicates otherwise.

In its first aspect, the invention is directed to proteins, except as existing in nature, comprising the amino acid sequence consisting functionally of rat GAL-R2 (as shown in FIG. 1) or consisting functionally of human GAL-R2 (as shown in FIG. 2). The term "consisting functionally of" refers to proteins in which the sequence of FIG. 1 or FIG. 2 has undergone additions, deletions or substitutions which do not substantially alter the functional characteristics of the receptor. Thus, the invention encompasses proteins having exactly the same amino acid sequence as shown in the figures, as well as proteins with differences that are not substantial as evidenced by their retaining the basic, qualitative ligand binding properties of GAL-R2. The invention further encompasses substantially pure proteins consisting essentially of a GAL-R2 amino acid sequence, antibodies that bind specifically to GAL-R2 (i.e. that have at least a 100 fold greater affinity for GAL-R2 than any other protein), and antibodies made by a process involving the injection of pharmaceutically acceptable preparations of such proteins into an animal capable of antibody production. In a preferred embodiment, monoclonal antibody to GAL-R2 is produced by injecting the pharmaceutically acceptable preparation of GAL-R2 into a mouse and then fusing mouse spleen cells with myeloma cells.

The invention is also directed to a substantially pure polynucleotide encoding a protein comprising the amino acid sequence consisting functionally of the sequence of rat GAL-R2 (as shown in FIG. 1) or human GAL-R2 (as shown in FIG. 2). This aspect of the invention encompasses polynucleotides encoding proteins consisting essentially of the amino acid sequences of in the figures, expression vectors comprising such polynucleotides, and host cells transformed with such vectors. Also included is the recombinant rat and human GAL-R2 proteins produced by host cells made in this manner. Preferably, the polynucleotide encoding rat GAL-R2 has the nucleotide sequence shown in FIG. 1 and the polynucleotide encoding human GAL-R2 has the nucleotide sequence shown in FIG. 2. It is also preferred that the vectors and host cells used for the expression of GAL-R2 use these particular polynucleotides.

In another aspect, the present invention is directed to a method for assaying a test compound for its ability to bind to GAL-R2. This method is performed by incubating a source of GAL-R2 with a ligand known to bind to the receptor and with the test compound. The source of GAL-R2 should be substantially free of other types of galanin receptors, i.e. greater than 90% of the galanin receptors present should correspond to GAL-R2. Upon completion of incubation, the ability of the test compound to bind to GAL-R2 is determined by the extent to which ligand binding has been displaced. A preferred source of GAL-R2 for use in the assay is a cell transformed with a vector for expressing the receptor and comprising a polynucleotide encoding a protein consisting essentially of the amino acid sequence shown in FIG. 1 (rat GAL-R2) and FIG. 2 (human GAL-R2). Instead of using cells in the assay, a membrane preparation can be prepared from the cells and this can be used as the source of GAL-R2. Although not essential, the assay can be accompanied by the determination of the activation of a second messenger pathway such as the adenyl cyclase pathway. This should help to determine whether a compound that binds to GAL-R2 is acting as an agonist or antagonist to galanin.

In another aspect, the present invention is directed to a method for assaying a test compound for its ability to alter the expression of GAL-R2. This method is performed by growing cells expressing GAL-R2, but substantially free of other galanin receptors, in the presence of the test compound. Cells are then collected and the expression of GAL-R2 is compared with expression in control cells grown under essentially identical conditions but in the absence of the test compound. In preferred embodiments, the cells expressing GAL-R2 are cells transformed with an expression vector comprising a polynucleotide sequence encoding a protein consisting essentially of the amino acid sequence shown in FIG. 1 (rat GAL-R2) or FIG. 2 (human GAL-R2). A preferred test compound is an oligonucleotide at least 15 nucleotides in length and comprising a sequence complimentary to a sequence shown in one or both of the figures. The preferred method for determining receptor expression is by means of a receptor binding assay.

BRIEF DESCRIPTION OF THE DRAWINGS

FIGS. 1A–1D: The composite nucleotide sequence and corresponding translated amino acid sequence (in single letter code) of rat GAL-R2 is shown. The nucleic acid sequence has been given the designation SEQ ID NO:1 and the amino acid sequence, SEQ ID NO:2.

FIGS. 2A–2C: The composite nucleotide sequence and corresponding translated amino acid sequence (in single letter code) of human GAL-R2 is shown. The nucleic acid sequence has been given the designation SEQ ID NO:3 and the amino acid sequence, SEQ ID NO:4.

FIGS. 3A–3B: The amino acid sequences of rat GAL-R2 (RGALR2.PRO), rat GAL-R1(rGALR1.PRO), human GAL-R2(HGALR2.PRO) and human GAL-R1 (hGALR1.PRO) are aligned to show regions of homology. The residues in the HGAL-R2 sequence that are shared with other sequences are boxed. In order to optimize alignment, gaps were created at several places in GAL-R2 sequences and these gaps are indicated by black boxes. The rGALR1.PRO sequence has been designated as SEQ ID NO:5; and the hGALR1.PRO sequence as SEQ ID NO:6.

FIG. 4 shows the results of binding assays in which unlabeled galanin and galanin-related peptides were allowed to compete with labeled galanin for GAL-R2 sites. The data has been converted to percentages, with binding in the absence of competitor serving as 100%. No inhibition was observed when binding assays were performed in the presence of peptides unrelated to galanin.

DEFINITIONS

Figure 4:
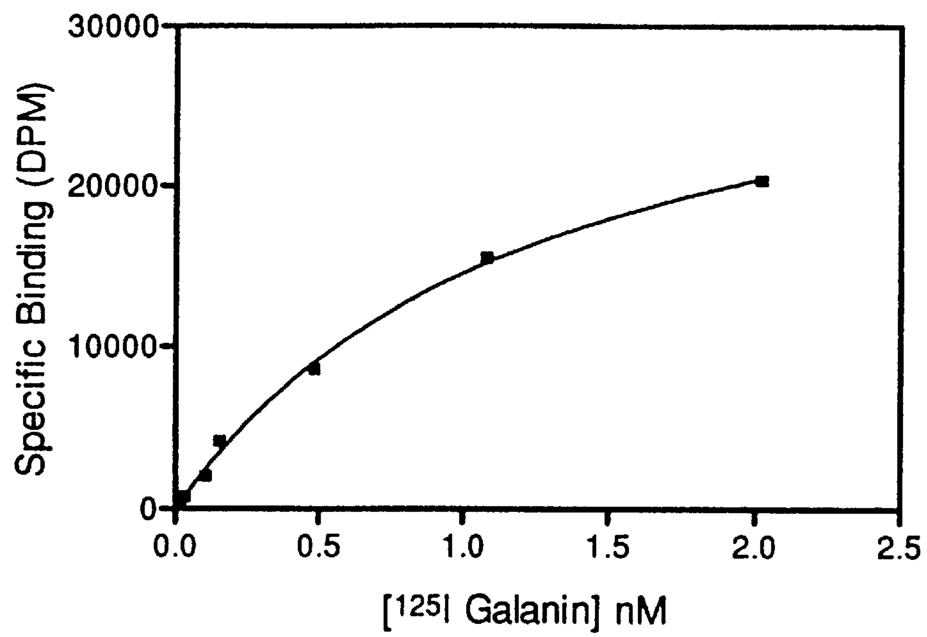
FIG. 4: The saturation isotherm of $^{125}$I-galanin binding to membranes from rat GAL-R2-expressing HEK-293 cells is shown. Increasing concentrations of radiotracer were incubated with the membranes, binding was allowed to reach equilibrium, and then the reaction was filtered as described under Example 3. Nonspecific binding was measured in the presence of 1 $\mu$M of unlabeled galanin and was subtracted from total binding to obtain specific binding.

The description that follows uses a number of terms that refer to recombinant DNA technology. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain a marker suitable for use in the identification of transformed cells. For example, markers may provide tetracycline resistance or ampicillin resistance.

Expression vector: A vector similar to a cloning vector but which is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

Substantially pure: As used herein, "substantially pure" means that the desired product is essentially free from contaminating cellular components. Contaminants may include, but are not limited to, proteins, carbohydrates or lipids. One method for determining the purity of a protein or nucleic acid is by electrophoresing a preparation in a matrix such as polyacrylamide or agarose. Purity is evidenced by the appearance of a single band after staining.

Host: Any prokaryotic or eukaryotic cell that is the recipient of a replicable expression vector or cloning vector is the"host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g. Sambrook et al., Molecular Cloning: A Laboratory Manual, 2nd ed. Cold Spring Harbor (1989)).

Promoter: A DNA sequence typically found in the 5' region of a gene, located proximal to the start codon. Transcription is initiated at the promoter. If the promoter is of the inducible type, then the rate of transcription increases in response to an inducing agent.

Complementary Nucleotide Sequence: A complementary nucleotide sequence, as used herein, refers to the sequence that would arise by normal base pairing. For example, the nucleotide sequence 5'-AGAC-3' would have the complementary sequence 5'-GTCT-3'. Expression: Expression is the process by which a polypeptide is produced from DNA. The process involves the transcription of the gene into mRNA and the translation of this mRNA into a polypeptide.

DETAILED DESCRIPTION OF THE INVENTION

The present invention is directed to the GAL-R2 receptor proteins, genetic sequences coding for the receptors, a method for assaying compounds for binding to GAL-R2 and a method for assaying compounds for their ability to alter GAL-R2 expression. The receptors and their nucleic acids are defined by their structures (as shown in FIGS. 1 and 2) as well as by their tissue distribution and binding characteristics.

With respect to structure, it will be understood that the present invention encompasses not only sequences identical to those shown in the figures, but also sequences that are essentially the same and sequences that are otherwise substantially the same and which result in a receptor retaining the basic binding characteristics of GAL-R2. For example, it is well known that techniques such as site-directed mutagenesis may be used to introduce variations in a protein's structure. Variations in GAL-R2 introduced by this or some similar method are encompassed by the invention provided that the resulting receptor retains the ability to specifically bind to galanin or galanin-like peptides. Thus, the invention relates to proteins comprising amino acid sequences consisting functionally of the sequence of SEQ ID NO:2 (rat) and SEQ ID NO:4 (human).

I. Nucleic Acid Sequences Coding for GAL-R2

DNA sequences coding for GAL-R2 are present in a variety of tissues, any of which may serve as a source for the isolation of nucleic acid coding for the receptor. In rats, spinal cord and brain tissues are among the preferred sources with the dorsal ganglia of the spinal cord and the hippocampus, mammillary bodies and cerebellum of the brain being especially preferred. In addition, cells and cell lines that express GAL-R2 may serve as a source for nucleic acid. These may either be cultured cells that have not undergone transformation or cell lines specifically engineered to express recombinant GAL-R2. Many methods are available for isolating DNA sequences and may be adapted for the isolation of GAL-R2 nucleic acid (see for example Sambrook et al., Molecular Cloning: A Laboratory Manual, 2nd ed., Cold Spring Harbor Press (1989)). One preferred method for rat GAL-R2, illustrated in Example 1, is to screen a cDNA library that has been prepared by reverse transcribing mRNA isolated from tissues or cells known to express GAL-R2. The library may be prepared from, for example, rat dorsal root ganglia or from brain tissue. A rat brain stem spinal cord cDNA library in ZAP II has been found to produce suitable results. A similar method can be used for human GAL-R2 or, alternatively, a human DNA library can be screened as described in Example 7.

It is expected that a wide variety of probes specific for GAL-R2 can be used equally well for the screening of cDNA libraries. One way to easily produce a large amount of probe is to use the polymerase chain reaction (PCR) to amplify the desired sequence from a cDNA library. For example, PCR may be performed on a cDNA library from rat dorsal root ganglia using the primers:

TM2: 5'-GGCCGTCGACTTCATCGTC(A or T)(A or C)(T or C)CTI(G or T)CI(T or C)TIGC(A,C,G or T)GAC-3' (SEQ ID NO:7)

TM7: 5'-(A or G)(C,A or T)(A or T)(A or G)CA(A or G)TAIATIATIGG(A or G)TT-3' (SEQ ID NO:8)

The letter"I" in the sequences above, is the abbreviation for inosine.

Amplified fragments can be size fractionated on an agarose gel and the selected fragments (e.g., fragments 400–1,000 base pairs in length) inserted into an appropriate vector (e.g., pGEM-T). The vector may be introduced into competent cells (e.g., DH5 cells) by any of the established methods for cell transformation, e.g., by calcium phosphate precipitation. Transformed cells containing the DNA of interest may be identified by again performing PCR with the TM2 and TM7 primers. The DNA inserts present in these cells are excised, purified and labeled with $^{32}P$. The labeled DNA fragments thus produced are used as probes for screening a cDNA library for GAL-R2. The presence of the correct sequence in selected cells may be confirmed by DNA sequencing and, if necessary, partial clones may be spliced together to form a full-length sequence.

Although the above procedure is known to be suitable for obtaining GAL-R2 nucleic acid, it is expected that alternative techniques can be developed with relatively little effort. Thus, cDNA libraries may be screened using probes synthesized based upon the GAL-R2 sequence shown in FIG. 1 for rats and shown in FIG. 2 for humans. In general, probes should be at least 14 nucleotides long and should not be selected from regions known to be highly conserved among proteins, e.g., the transmembrane domains of G-protein linked receptors. Alternatively, using the sequences shown in the figures, it should be possible to select PCR primers that amplify the full-length GAL-R2 sequence. The same techniques that have proven successful in the rat and human can be used to obtain GAL-R2 sequences from other species as well.

II. Production and Isolation of GAL-R2 Recombinant Protein

In order to express recombinant GAL-R2, the structural sequence for the protein described above must be placed in a vector containing transcriptional and translational signals recognizable by an appropriate host. The cloned GAL-R2 sequences, preferably in double-stranded form, are inserted into the expression vector in an operable linkage, i.e., they are positioned so as to be under the control of the vector's regulatory sequences and in such a manner that mRNA is produced which is translated into the GAL-R2 amino acid sequence.

Expression of the GAL-R2 receptor protein in different hosts may result in different post-translational modifications that can, potentially, alter the properties of the receptor. Preferably, nucleic acid encoding GAL-R2 is expressed in eukaryotic cells, especially mammalian cells. These cells provide post-translational modifications which, inter alia, aid in the correct folding of the receptor protein. Examples of an appropriate vector, pcDNA3-GAL-R2, and host, HEK293 cells, are given in the Example 2.

Other mammalian cells that may be used include, without limitation, NIH-3T3 cells, CHO 5 cells, HeLa cells, LM(tk-) cells etc. Vectors suitable for use in each of these various cell types are well known in the art (see e.g. Sambrook et al., supra). Preferred eukaryotic promoters include that of the mouse metallothionein I gene; the TK promoter of Herpes virus; the SV40 early promoter; and the yeast GAL4 gene promoter. Some examples of suitable prokaryotic promoters include those capable of recognizing T4 polymerases, the $P_R$ and $P_L$ promoters of bacteriophage lambda, and the trp, recA, heat shock and lacZ promoters of *E. coli.*

Expression vectors may be introduced into host cells by methods such as calcium phosphate precipitation, microinjection or electroporation. Cells expressing the GAL-R2 receptor can be selected using methods well known in the art. One simple method for confirming the presence of the receptor nucleic acid in cells is to perform PCR amplification using the procedures and primers discussed above. The presence of functional receptor may be confirmed by performing binding assays using labeled galanin.

Once cells producing recombinant GAL-R2 receptor have been identified, they may be used in either binding assays or in assays designed to identify agents capable of altering GAL-R2 expression. Alternatively, membranes may be isolated from the cells and used in receptor binding assays.

III. Antibodies to GAL-R2

The present invention also is directed to antibodies that bind specifically to GAL-R2 and to a process for producing such antibodies. Antibodies that "bind specifically to GAL- R2" are defined as those that have at least a one hundred fold greater affinity for GAL-R2 than for GAL-R1 and any undenatured protein not binding galanin. The process for producing such antibodies may involve either injecting the GAL-R2 protein itself into an appropriate animal or, preferably, injecting short peptides made to correspond to different regions of GAL-R2. The peptides should be at least five amino acids in length and should be selected from regions believed to be unique to the GAL-R2 protein. Thus, highly conserved transmembrane regions should generally be avoided in selecting peptides for the generation of antibodies. Methods for making and detecting antibodies are well known to those of skill in the art as evidenced by standard reference works such as: Harlow et al., Antibodies, A Laboratory Manual, Cold Spring Harbor Laboratory, N.Y. (1988)); Klein, Immunology: The Science of Self-Nonself Discrimination (1982); Kennett, et al., Monoclonal Antibodies and Hybridomas: A New Dimension in Biological Analyses (1980); and Campbell, "Monoclonal Antibody Technology," in Laboratory Techniques in Biochemistry and Molecular Biology, (1984)).

"Antibody," as used herein, is meant to include intact molecules as well as fragments which retain their ability to bind to antigen (e.g., Fab and $F(ab)_2$ fragments). These fragments are typically produced by proteolytically cleaving intact antibodies using enzymes such as papain (to produce Fab fragments) or pepsin (to produce $F(ab)_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in: Monoclonal Antibodies and T-Cell Hybridomas, Elsevier, M. Y., pp. 563–681 (1981)). In general, this technology involves immunizing an animal, usually a mouse, with either intact GAL-R2 or a fragment derived from GAL-R2. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding to GAL-R2.

The antibodies, or fragments of antibodies, of the present invention may be used to detect the presence of GAL-R2 protein using any of a variety of immunoassays. For example, the antibodies may be used in radioimmunoassays or in immunometric assays, also known as "two-site" or"sandwich" assays (see Chard, T., "An Introduction to Radioimmune Assay and Related Techniques," in Laboratory Techniques in Biochemistry and Molecular Biology, North Holland Publishing Co., N.Y. (1978)). In a typical immunometric assay, a quantity of unlabelled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see e.g. Radioimmune Assay Method, Kirkham et al., e.d., pp. 199–206, E & S. Livingstone, Edinburgh (1970)). Many variations of these types of assays are known in the art and may be employed for the detection of GAL-R2.

Antibodies to GAL-R2 may also be used in the purification of either the intact receptor or fragments of the receptor (see generally, Dean et al., Affinity Chromatography, A Practical Approach, IRL Press (1986)). Typically, antibody is immobilized on a chromatographic matrix such as Sepharose 4B. The matrix is then packed into a column and the preparation containing GAL-R2 is passed through under conditions that promote binding, e.g., under conditions of low salt. The column is then washed and bound GAL-R2 is eluted using a buffer that promotes dissociation from antibody, e.g., buffer having an altered pH or salt concentration. The eluted GAL-R2 may be transferred into a buffer of choice, e.g., by dialysis, and either stored or used directly.

IV. Assay for GAL-R2 Binding

One of the main uses for GAL-R2 nucleic acids and recombinant proteins is in assays designed to identify agents, other than galanin, capable of binding to GAL-R2 receptors. Such agents may either be agonists, mimicking the effects of galanin, or antagonists, inhibiting the effects of galanin. Of particular interest is the identification of agents which bind to the GAL-R2 receptors and modulate adenyl cyclase activity in the cells. These agents have potential therapeutic application as either analgesics or anesthetics.

An example of an assay that may be used for detecting compounds binding to GAL-R2 is presented in Example 4. The essential feature of this assay is that a source of GAL-R2 is incubated together with a ligand known to bind to the receptor and with the compound being tested for binding activity. The preferred source for GAL-R2 is cells, preferably mammalian cells, transformed to recombinantly express the receptor. The cells selected should not express a substantial amount of any other receptor which binds galanin, e.g., GAL-R1. This can easily be determined by performing galanin binding assays on cells derived from the same tissue or cell line as those recombinantly expressing GAL-R2 but which have not undergone transformation.

The assay may be performed either with intact cells or, preferably, with membranes prepared from the cells (see e.g. Wang, et al., *Proc. Natl. Acad. Sci. U.S.A.* 90:10230–10234 (1993)). The membranes are incubated with a ligand specific for galanin receptors and with a preparation of the compound being tested. After binding is complete, receptor is separated from the solution containing ligand and test compound, e.g. by filtration, and the amount of binding that has occurred is determined. Preferably, the ligand used is galanin detectably labeled with a radioisotope such as $^{125}I$. However, if desired, fluorescent or chemiluminescent labels can be used instead. Among the most commonly used fluorescent labeling compounds are fluorescein isothiocynate, rhodamine, phycoerythrin, phycocyanin, allophycocyanin, o-phthaldehyde and fluorescamine. Useful chemiluminescent compounds include luminol, isoluminol, theromatic acridinium ester, imidazole, acridinium salt, and oxalate ester. Any of these agents which can be used to detectably label galanin will produce a ligand suitable for use in the assay.

Nonspecific binding may be determined by carrying out the binding reaction in the presence of a large excess of unlabelled ligand. For example, $^{125}I$-galanin may be incubated with receptor and test compound in the presence of a thousandfold excess of unlabelled galanin. Nonspecific binding should be subtracted from total binding, i.e. binding in the absence of unlabeled galanin, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced galanin.

Figure 5:
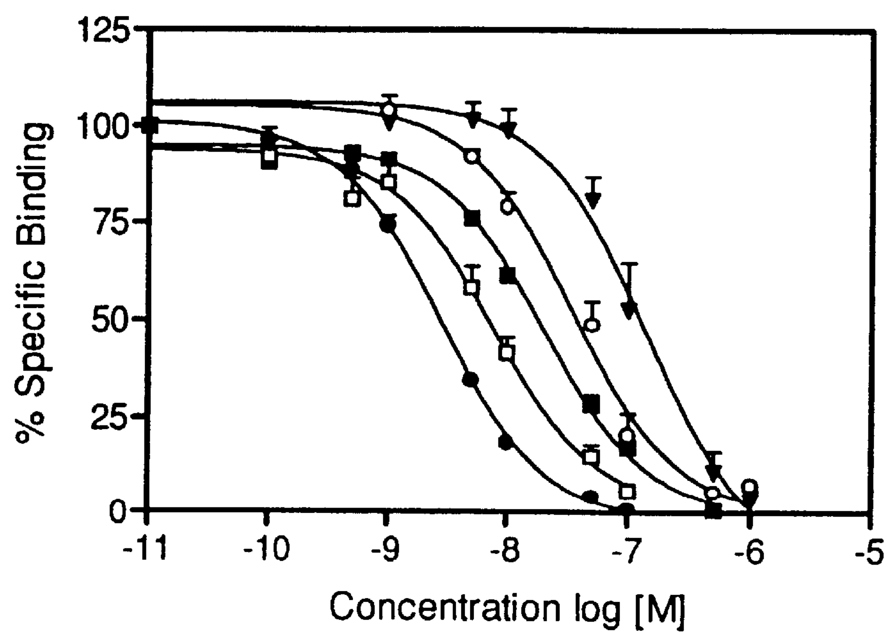
FIG. 5.

In performing binding assays, care must be taken to avoid artifacts which may make it appear that a test compound is interacting with the GAL-R2 receptor when, in fact, binding is being inhibited by some other mechanism. For example, the compound being tested should be in a buffer which does not itself substantially inhibit the binding of galanin to GAL-R2 and should, preferably, be tested at several different concentrations. Preparations of test compound should also be examined for proteolytic activity and it is desirable that antiproteases be included in assays. Finally, it is highly desirable that compounds identified as displacing the binding of ligand to GAL-R2 receptor be reexamined in a concentration range sufficient to perform a Scatchard analysis on the results. This type of analysis is well known in the art and can be used for determining the affinity of a test compounds for receptor (see e.g., Ausubel, et al., Current Protocols in Molecular Biology, 11.2.1–11.2.19 (1993); Laboratory Techniques and Biochemistry and Molecular Biology, Work, et al., ed., N.Y. (1978) etc.). Computer programs may be used to help in the analysis of results (see e.g., Munson, P., *Methods Enzymol.* 92:543–577 (1983); McPherson, G. A., Kinetic, EBDA Ligand, Lowry-A Collection of Radioligand Binding Analysis Programs, Elsevier-Biosoft, U.K. (1985)). An example of the types of curves that may be obtained using this method is shown in FIG. 5 and examples of inhibitory constants for galanin-related peptides deter-mined using binding assays are shown in Table 1.

The activation of a second messenger pathway may be examined by performing adenyl cyclase assays for compounds that have been identified as binding to the GAL-R2 receptor. These assays may be carried out as discussed in Example 5 or using any other method for determining cAMP concentration. Typically, adenyl cyclase assays will be performed separately from binding assays, but it may also be possible to perform binding and adenyl cyclase assays on a single preparation of cells.

V. Assay for Ability to Modulate GAL-R2 Expression

One way to either increase or decrease the biological effects of galanin is to alter the extent to which GAL-R2 is expressed in cells. Therefore, assays for the identification of compounds that either inhibit or enhance expression are of considerable interest. These assays are carried out by growing cells expressing GAL-R2 in the presence of a test compound and then comparing receptor expression in these cells with cells grown under essentially identical conditions but in the absence of the test compound. As in the binding assays discussed above, it is desirable that the cells used be substantially free of receptors for galanin other than GAL-R2. Scatchard analysis of binding assays performed with labeled galanin can be used to determine receptor number. The binding assays may be carried out as discussed above in section IV and will preferably utilize cells that have been engineered to recombinantly express GAL-R2 as described in sections I and II. A preferred group of test compounds for inclusion in the GAL-R2 expression assay consists of oligonucleotides complementary to various segments of the GAL-R2 nucleic acid sequence. These oligonucleotides should be at least 15 bases in length and should be derived from non-conserved regions of the receptor nucleic acid sequence.

Oligonucleotides which are found to reduce receptor expression may be derivatized or conjugated in order to increase their effectiveness. For example, nucleoside phosphoro-thioates may be substituted for their natural counterparts (see Cohen, J., Oligodeoxy-nucleotides, Anti-sense Inhibitors of Gene Expression, CRC Press (1989)). The oligo-nucleotides may be delivered to a patient in vivo for the purpose of inhibiting GAL-R2 expression. When this is done, it is preferred that the oligonucleotide be administered in a form that enhances its uptake by cells. For example, the oligonucleotide may be delivered by means of a liposome or conjugated to a peptide that is ingested by cells (see e.g., U.S. Pat. Nos. 4,897,355 and 4,394,448; see also non-U.S. patent documents WO 8903849 and EP 0263740). Other methods for enhancing the efficiency of oligonucleotide delivery are well known in the art and are also compatible with the present invention.

Having now described the invention, the same will be more readily understood through reference to the following Examples which are provided by way of illustration and which are not intended to limit the scope of the invention.

EXAMPLES

Example 1

Cloning of Rat Galanin Receptor-2 (GAL-R2)

A PCR-based homology screening strategy was used to isolate novel cDNA sequences encoding G protein-coupled receptors. Sequences likely to encode G protein-coupled receptors were amplified from rat dorsal root ganglia mRNA by reverse transcription PCR using the following primers:

TM2: 5'-GGCCGTCGACTTCATCGTC(A or T)(A or C)(T or C)CTI(G or T)CI(T or C)TIGC(A,C,G or T)GAC-3' (SEQ ID NO:5)

TM7: 5'-(A or G)(C,A or T)(A or T)(A or G)CA(A or G)TAIATIATIGG(A or G)TT-3' (SEQ ID NO:6)

The templates for PCR amplification were synthesized using a"First Strand cDNA Synthesis Kit" (Pharmacia Biotech) and 400 ng of dorsal root ganglia poly A+RNA. The first strand cDNA thus prepared was diluted two fold with distilled water, heated at 95 C for 3 minutes and quickly chilled on ice. 5 $\mu$L of the cDNA thus produced was then amplified with 50 pmoles of each of the TM2 and TM7 primers and 2.5 units of Taq DNA polymerase in 50 mM KCl, 1.5 mM $MgCl_2$, 10 mM Tris(HCl), and 200 $\mu$M dNTPs, pH 9.0. The reaction tubes were heated at 95° C. for one min. and then subjected to 40 cycles of denaturation (95° C./1 min), annealing (45° C./1 min) and extension (72° C./1 min). The final extension was performed for 10 min. The amplified fragments were analyzed and size fractionated on a 1.5% agarose gel. Fragments between 400 bp and 1000 bp in length were excised from the gel, purified using a Sephaglas BandPrep kit from Pharmacia, and inserted into a pGEM-T vector from Promega. The recombinant plasmids thus produced were used to transform competent DH5 cells.

Transformed cells were plated on ampicilline-containing 2YT agar plates and recombinant pGEM-T clones were selected by direct colony PCR using primers designed for T7 and SP6 promoters. The PCR conditions were exactly the same as above except 50 pmole each of T7 and SP6 primers were used instead of TM2 and TM7 primers. The annealing temperature was 50 C. and 30 cycles were performed. Plasmid DNA was prepared from the clones containing recombinant plasmids using a"Wizard Miniprep DNA Purification System" (Promega Corporation) starting with 4 ml of bacterial culture. The DNA sequence from these clones was determined using the Sanger dideoxynucleotide chain termination method on denatured double-stranded plasmid templates using a T7 sequencing kit from Pharmacia.

The insert DNA fragment of clone 3B-21 was excised from the vector using Sac II and Nde I, isolated on an agarose gel and labeled with $^{32}P$ by random primed synthesis using a Ready-To-Go DNA labeling kit from Pharmacia. This labeled fragment was used to screen a rat brain stem spinal cord cDNA library in ZAP II (Stratagene). Filters were prehybridized for 2 hours at 42° C. in 50% formamide, 5×SSC, 5×Denhardt's solution, 1% glycine and 100 μg/ml denatured and sheared salmon sperm DNA. Hybridization with labeled probe was performed at 42 C. for 18 hours in a solution containing 50% formamide, 5×SSC, 1×Denhardt's solution, 0.3% SDS and 100 μg/ml denatured and sheared salmon sperm DNA. Filters were rinsed twice in 2×SSC, 0.1% SDS at room temperature. They were then washed twice for 15 min in 2×SSC, 0.1% SDS at 42 C., twice for 15 min at 42 C. in 0.2×SSC, 0.1% SDS, twice with 0.05×SSC, 0.1% SDS at 55 C. and finally in the same wash solution at 65 C.

Hybridization-positive phages were purified and their inserts rescued by helper phage mediated excision to yield plasmid DNAs. One clone, 21RSC4, contained the complete coding sequence for the receptor except for 51 bp of the 5' region. This region was obtained by PCR and was then joined at the Bsu36I site at nucleotide number 16 of 21RSC4. Thus, 67 bp at the 5'-end of the coding region of the clone pBS/GALR-2 arose from a PCR-generated fragment.

Example 2

Structural Characteristics of Rat Galanin Receptor-2

The recombinant plasmid pBS/GALR-2 was found to contain an open reading frame of 372 amino acids, flanked by 3' and 5' untranslated regions of, respectively, 289 and 308 bp. The sequence of the open reading frame is shown in FIG. 1 along with the amino acid sequence of the encoded protein. The protein has a molecular mass of 40,700 daltons. Hydropathy analysis of the protein is consistent with a topography of seven transmembrane domains, indicative of the G-protein-coupled receptor family (Sprengel et al., "Hormone Receptors," in Handbook of Receptors and Channels: G Protein-Coupled Receptors, Peroutka, S. J., ed., pp. 153–207, CRC Press (1994)). In addition, sequence analysis revealed that the open reading frame of pBS/GALR-2 contains several conserved structural features/residues found among the members of the neuropeptide receptor family, including: an asparagine in TM1 (Asn43); a leucine (Leu67) and an aspartic acid (Asp 71) in TM2; and an arginine (Arg123) and Tyrosine residue (Tyr124) in TM3. Other features of this GAL-R2 receptor gene are: potential sites for N-glycosylation in the amino terminus (Asn2, Asn11); the presence of several serines and threonines in the carboxyl terminus; and the presence of a second and third intracellular loop, which may serve as potential sites for phosphorylation by protein kinases.

A comparison of the rat GAL-R2 open reading frame with the sequences of human GAL-R2 and GAL-R1 receptors is shown in FIG. 3. Overall, rat GAL-R2 has an identity of about 53% at the nucleotide level and 35.5% at the amino acid level with rat GAL-R1 (Burgevin et al., *J. Mol. Neurosci*. 6:33–41 (1995)) and 34.8% with human GAL-R1 (Habert-Ortoli et al., *Proc. Natl. Acad. Sci. USA* 919780–9783 (1994)). However the sequence homology is higher in the putative transmembrane domains. Respectively, the homologies between the known rat GAL-R1 and GAL-R2 in TM1 to TM7 are 37.5%, 67%, 41.6%, 25%, 50%, 33% and 50%.

Overall, it is apparent that GAL-R2 has a unique sequence that sets it apart from the other G-protein-coupled receptors or other members of the neuropeptide receptor subfamily. The amino acid residues essential for the binding of galanin to the GAL-R1 receptor have been identified as His264, His267, Phe282 and, to a lesser extent, Glu271. Only one of these residues, corresponding to His264, is conserved in GAL-R2.

Example 3

Recombinant Expression of Rat Galanin Receptor-2

To generate a mammalian expression vector, a 1.4 Kb Hind III-Bst-XI restriction fragment from pBS/GALR-2 was isolated and subcloned between the Hind III and BstX-I sites of pcDNA3 from InVitrogen, San Diego, Calif. This expression vector, designated pcDNA3/GALR-2, contains, in addition to the entire receptor coding sequence, 50 bp of 5' untranslated sequence and 288 bp of 3' untranslated sequence. Plasmid DNA for further analysis was prepared using the Qiaprep system from Qiagen.

A. Transient Transfection

HEK293s cells were obtained from Cold Spring Harbor laboratory. They were maintained in culture medium at 37° C., 5% $CO_2$ and diluted 10 fold every 3 days. The cells were inoculated in 80 $cm^2$ flasks (2×106 cells per flask) in Dulbeco's Modified Essential Medium (DMEM, Gibco BRL), supplemented with 10% fetal bovine serum (FBS), 100 U/ml penicillin, 100 μg/ml streptomycin and 0.25 μg/ml fungizone. One day after inoculation, cells were transiently transfected using a modified $CaCl_2$ method (Maniatis, Molecular Cloning: A Laboratory Manual, Cold Spring Harbor Laboratory Press (1989)) and 30 μg of plasmid DNA per flask. The cells were harvested 48 hours post transfection for ligand binding or signal transduction experiments.

B. Stable Transfection

HEK293s cells in 80 $cm^2$ flasks were transfected with 30 μg pcDNA3/GALR-2. After 21 days of selection in culture medium containing 600 μg/ml G418 resistant colonies were pooled and expanded for the radioligand binding and signal transduction studies.

Example 4

Binding Characteristics of Recombinantly Expressed Rat GAL-R2

A. Methods

A galanin binding assay was performed on the crude membranes prepared from pcDNA3/GALR-2 transfected cells. The cells were grown in 150 mm petri dishes to about 80% confluency. Before harvesting, the cells on the petri dishes were washed once with cold PBS (Gibco BRL). Cells were then scraped in ice cold PBS using a Teflon cell scraper. The cells thus harvested were gently centrifuged at 1500×g at 4 C., resuspended in membrane buffer, "MB" (20 mM HEPES pH 7.5 containing 10 μg/ml benzamidine, 5 μg/ml leupeptin, 5 μg/ml soybean trypsin inhibitor and 0.1 mM phenyl methyl sulfonyl fluoride) and were disrupted with a Polytron at a setting of ~20,000 rpm for 30 sec. The disrupted cell suspension was centrifuged at ~100,000×g for 60 minutes at 4 C. using a fixed angle rotor in a Beckman L8-70M Ultracentrifuge. The pellet thus obtained was resuspended in the membrane buffer at a concentration of 1.0~1.5 mg/ml, aliquoted and frozen at −80 C. until used.

The binding reaction was performed in a total volume of 100 μl of binding buffer (MB+0.4% bovine serum albumin) containing 5–10 μg membrane protein and 0.1 nM $^{125}$I- galanin (2200 Ci/mmol, Dupont/NEN) with or without unlabeled competitors. Non-specific binding was estimated in the presence of 1 μM of unlabeled galanin. Binding reactions proceeded for 20 min at room temperature and were stopped by filtration through Unifilters-96, GF/B filters (Canberra Packard), using the 96-well Filtermate 196 filtration system from Canberra Packard. Filters were washed 5 times with 0.5 ml of ice cold 20 mM HEPES pH 7.5. The filters were dried at 55° C. for one hour and then 100 μl of μScint-20 (Canberra Packard) was added per well. Filters were counted with the Topcount microplate counter from Canberra Packard.

B. Results

When transfected into HEK293 cells, pcDNA3/GALR-2 resulted in the expression of specific $^{125}$I-galanin binding sites. No specific $^{125}$I-galanin binding sites were generated by the transfection of the vector itself or a control pcDNA3 expression construct encoding a delta-opioid receptor. A pool of stable HEK293 cells expressing the GAL-R2 receptor was generated by selecting pcDNA3/GALR-2 transfected cells using G418 and binding experiments were performed on the membranes of these cells. An example of the results from a binding experiment is shown in FIG. 4.

A single class of saturable $^{125}$I-galanin binding site was detected with an estimated Kd for $^{125}$I-galanin of 1.68±0.43 nM and a Bmax of 1–2 pmol/mg of crude protein. Various galanin related peptides were used in competition experiments performed using $^{125}$I-galanin as a tracer. The competition curves for these peptides are displayed in FIG. 5 and the Ki values of the peptides tested are summarized in Table 1.

TABLE 1

The inhibitory constants of galanin-related peptides for $^{125}$I-galanin binding at GAL-R2

| PEPTIDE | Ki [M] |
|---|---|
| Galanin | $2.65 \pm 0.07 \cdot 10^{-9}$ |
| Galanin(1–16) | $1.23 \pm 0.70 \cdot 10^{-8}$ |
| M15 | $3.68 \pm 1.20 \cdot 10^{-8}$ |
| M40 | $8.30 \pm 0.49 \cdot 10^{-9}$ |
| C7 | $1.89 \pm 1.34 \cdot 10^{-7}$ |

The binding of labeled galanin was displaced by galanin and galanin related peptides but not by galanin unrelated ligands (e.g. substance P, vasoactive intestinal polypeptide, angiotensin II and dynorphin). The main difference between rat GAL-R1 and GAL-R2, however, lies in the recognition of the chimeric peptide C7, which is equipotent to galanin at the GAL-R1 receptor but is much less active at GAL-R2.

Example 5

Activation of cAMP

Stable pools of transfected cells were inoculated in 24 well plates and allowed to grow overnight. Before experiments, the cells were washed with PBS at 37 C. and then covered with PBS containing 1 mM 3-isobutyl-1-methylxanthine (IBMX). Cells in duplicate wells were stimulated for 10 minutes at 37 C. either with forskolin (0.1 mM) alone, or in the presence of various concentrations of galanin or galanin-related peptides. cAMP was extracted in ethanol, lyophilized and resuspended in 0.5 mM assay buffer. Assay of cAMP was performed using either the Biotrack cAMP Enzyme-immunoassay System (Amersham) or the Cyclic AMP [$^3$H] Assay System (Amersham).

Figure 6A:
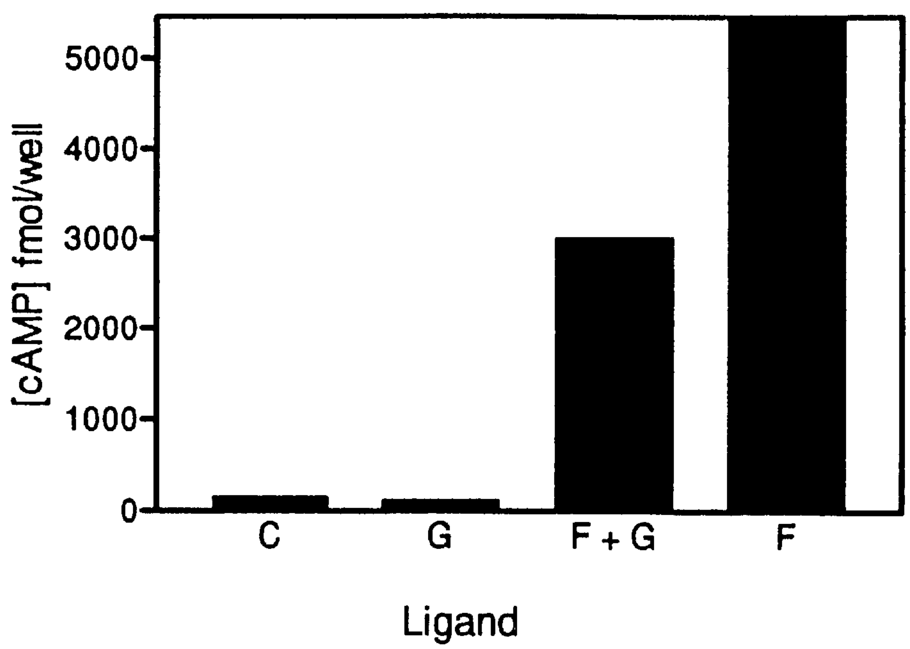
FIGS. 6A–6B: Galanin attenuated the stimulation of adenyl cyclase by forskolin in a dose-dependent manner in HEK-293 cells expressing GAL-R2. Panel A shows the basal level of cAMP in cells not treated with either forskolin or galanin (C); the effect of 1 $\mu$M galanin (G); the effect of 0.1 mM forskolin (F); and the effect of 1 $\mu$M galanin +0.1 mM forskolin (F+G). In panel B, cells were incubated in the presence of 0.1 mM forskolin alone or in the presence of forskolin with various concentrations of galanin. Intracellular cAMP was then extracted and measured by enzyme immunoassay as described in Example 4. Results are expressed as percentages, where 100% is the value obtained in the presence of forskolin alone.
Figure 6B:
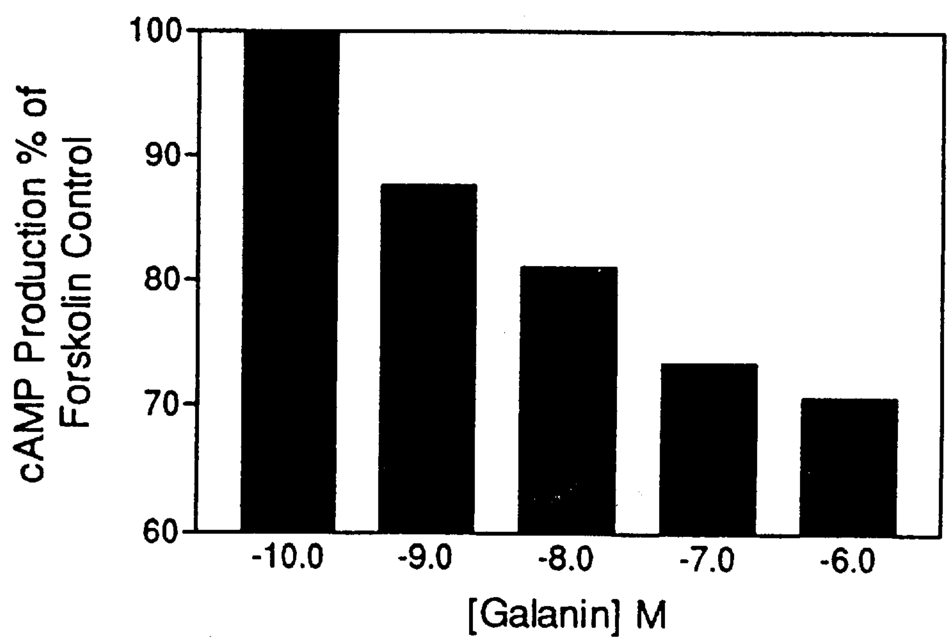

It was found that the activation of rat GAL-R2 in stably transfected HEK293 cells leads to a significant inhibition of forskolin-stimulated accumulation of cAMP and that this inhibition occurs in a concentration-dependent manner (FIG. 6). Untransfected cells failed to exhibit this effect.

Example 6

In Situ Hybridization

A. Methods

Adult male Sprague-Dawley rats (~300 gm; Charles River, St-Constant, Quebec) were sacrificed by decapitation. Brain, pituitary and spinal cord were promptly removed, snap-frozen in isopentane at −40 C. for 20 s and stored at −80 C. Frozen tissue was sectioned at 14 μm in a Microm HM 500 M cryostat (Germany) and thaw-mounted onto ProbeOn Plus slides (Fisher Scientific, Montreal, Quebec). Sections were stored at −80 C prior to in situ hybridization.

The plasmid pcDNA3-GALR-2 was linearized using either XbaI or HindIII restriction enzymes which cut in the polylinker on either side of the inserted cDNA. Sense and antisense GAL-R2 riboprobes were transcribed in vitro using either T7 or SP6 RNA polymerases (Pharmacia Biotech), in the presence of [$^{35}$S]UTP (~800 Ci/mmol; Amersham, Oakville, Ontario). Following transcription, the DNA template was digested with DNAse I (Pharmacia). Riboprobes were subsequently purified by phenol/chloroform/isoamyl alcohol extraction and precipitated in 70% ethanol containing ammonium acetate and tRNA. The quality of labeled riboprobes was verified by polyacrylamnide-urea gel electrophoresis.

Sections were postfixed in 4% paraformaldehyde (BDH, Poole, England) in 0.1 M phosphate buffer (pH 7.4) for 10 min at room temperature (RT) and rinsed in 3 changes of 2×standard sodium citrate buffer (SSC: 0.15 M NaCl. 0.015 M sodium citrate, pH 7.0). Sections were then equilibrated in 0.1 M triethanolamine, treated with 0.25% acetic anhydride in triethanolamine, rinsed in 2×SSC and dehydrated in an ethanol series (50–100%). Hybridization was performed in a buffer containing 75% formamide, 600 mM NaCl, 10 mM Tris (pH 7.5), 1 mM EDTA, 1×Denhardt's solution, 50 mg/ml denatured salmon sperm DNA, 50 mg/ml yeast tRNA, 10% dextran sulfate, 20 mM dithiothreitol and [$^{35}$S] UTP-labeled cRNA probes ($10 \times 10^6$ cpm/ml) at 55 C for 18 h in humidified chambers. Following hybridization, slides were rinsed in 2×SSC at RT, treated with 20 mg/ml RNase IA in RNase buffer (10 mM Tris, 500 mM NaCl, 1 mM EDTA, pH 7.5) for 45 min at RT and washed to a final stringency of 0.1×SSC at 65 C. Sections were then dehydrated and exposed to Kodak Biomax MR film for 10 days and/or dipped in Kodak NTB2 emulsion diluted 1:1 with distilled water and exposed for 3–4 weeks at 4 C. prior to development and counterstaining with cresyl violet acetate. Neuroanatomical structures were identified according to the Paxinos and Watson rat brain atlas (Paxinos et al., The Rat Brain in Stereotaxic Coordinates, Academic Press, N.Y. (1986)).

B. Results

The highest levels of rat GAL-R2 mRNA expression were observed in dorsal root ganglia with large, intermediate and small diameter cells being specifically labeled. Only diffuse labeling was observed throughout the dorsal and ventral horns of the spinal cord. In the rat brain, the highest densities of GAL-R2 mRNA labeling were detected in the dorsal hippocampus, mammillary bodies and cerebellum (in particular, Purkinje cell layer). More moderate labeling was detected in the pontine nucleus as well as in a specific cranial motor nucleus. Moderate to weak hybridization was detected throughout the cerebral cortices. Other cephalic areas such as the thalamus, the remaining hypothalamus, and basal ganglia were generally devoid of labeling. This distribution differs considerably from that reported for GALR-1 mRNA which is particularly well expressed in the ventral hippocampus, amygdala, supraoptic nucleus, several hypothalamic and thalamic nuclei, lateral parabrachial nucleus and locus coeruleus of rat brain.

The high level of GAL-R2 expression observed in dorsal root ganglia sensory neurons and more moderate levels observed in dorsal horn of the spinal cord is consistent with galanin's role in pain transmission. The presence of high levels of GAL-R2 in dorsal hippocampus and mammillary bodies is consistent with a role in cognitive function.

Example 7

Cloning and Structural Features of Human Galanin Receptor-2

A human genomic DNA library prepared from human placenta (Clonetech) in EMBL-3 vector was screened with a random labeled fragment (labeled with T7-Quick-Prime labeling kit cat. #27-9252-01, Pharmacia Biotech.) containing the complete coding region of rat GALR-2 cDNA. The prehybridization and hybridization conditions were as follows:

Prehybridization: 50% formamide, 5×Denhardt's solution, 5×SSC, 1% glycine, 100 g/ml sheared and denatured salmon sperm DNA at 42° C. for 5 hours.

Hybridization: 50% formamide, 1×Denhardt's solution, 5×SSC, 0.3% SDS, 100 g/ml sheared and denatured salmon sperm DNA overnight at 42° C.

Wash: A wash step was performed from the low stringency of 2×SSC, 0.1% SDS at 42° C. to the highest stringency of 0.2×SSC, 0.1% SDS at 60° C. (65° C. for Southern blots).

Eight positive clones were identified which were processed for secondary screening under hybridization and washing conditions identical to the first. The secondary screening resulted in identification of four clones; the other four clones were considered false-positive. The four positive clones were processed for tertiary and quarternary screening in order to obtain pure clones.

DNA was purified from the four pure clones discussed above and was processed for restriction analysis and Southern blot hybridization in order to identify smaller fragments which yield a positive signal. Three positively hybridizing bands (of estimated sizes ~5 kb, ~3.2 kb and ~0.7 kb) generated by the cleavage with Sac I and Rsa I restriction endonucleases (Pharmacia Biotech.) were identified by Southern blot hybridization. These bands were excised from the gel and subcloned into either Sac I or Eco RV digested pBlueScript KS(-) plasmid. The plasmid constructs were subjected to sequencing by Sanger dideoxy sequencing method (T7 Sequencing kit, Pharmacia Biotech. Cat. #27-1682-01) and the ABI Prizm Cycle Sequencing Kit (Cat. #402079, Perkin-Elmer) and the composite sequence was constructed.

The nucleotide sequence for human GALR-2 gene is depicted in FIG. 2. An open reading frame of 1155 nucleotides is present putatively encoding a protein of 385 amino acids with a calculated molecular mass of 41478 kD. There is a putative intron of more than 1000 nucleotide in length after base number 420. The intronic sequence has been removed from the finalized sequence reproduced in FIG. 2. The exon-intron boundaries were determined based upon the consensus sequences around 5' and 3' splice sites in vertebrate pre-mRNAs (Lodish et al. Molecular Cell Biology 3$^{rd}$ Ed. Scientific American Books, pp 500; FIG. 4.) At the protein level, 84.4% amino acids are identical between rat and human GALR-2; the identity between the human GALR-2 and the rat or human GALR-1 is about 34%.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

DEPOSIT OF BIOLOGICAL MATERIAL

The plasmid HUMAN GALR-2 has been deposited under the Budapest Treaty at "Deutsche Sammlung von Mikroorganismen und Zellkulturen" (DSMZ), Braunschweig, Germany. The deposit number is DSM 11632, and the date of deposit is Jun. 26, 1997.

What is claimed is:

1. A protein, except as existing in nature, consisting essentially of the rat GAL-R2 amino acid sequence as shown in SEQ ID NO:2.

2. A substantially pure protein according to claim 1, wherein said amino acid sequence consists of the amino acid sequence of SEQ ID NO:2.

3. A protein, except as existing in nature, consisting essentially of the human GAL-R2 amino acid sequence as shown in SEQ ID NO:4.

4. A substantially pure protein according to claim 3, wherein said amino acid sequence consists of the amino acid sequence of SEQ ID NO:4.

5. Recombinant rat GAL-R2 produced by a host cell transformed with a vector for expressing said rat GAL-R2, wherein said vector comprises a polynucleotide encoding a protein consisting essentially of the rat GAL-R2 amino acid sequence as shown in SEQ ID NO:2.

6. The recombinant rat GAL-R2 of claim 5, wherein said amino acid sequence consists of the sequence of SEQ ID NO:2.

7. Recombinant human GAL-R2 produced by a host cell transformed with a vector for expressing said human GAL-R2, wherein said vector comprises a polynucleotide encoding a protein consisting essentially of the human GAL-R2 amino acid sequence as shown in SEQ ID NO:4.

8. The recombinant human GAL-R2 of claim 7, wherein said amino acid sequence consists of the sequence of SEQ ID NO:4.

* * * * *

UNITED STATES PATENT AND TRADEMARK OFFICE

CERTIFICATE OF CORRECTION

PATENT NO. : 6,562,945 B1
DATED : May 13, 2003
INVENTOR(S) : Shen et al.

It is certified that error appears in the above-identified patent and that said Letters Patent is hereby corrected as shown below:

Title page,
Item [75], Inventor, "Shen Shi-Hsiang" should be -- Shi-Hsiang Shen --; and Inventor "Ahmad Sultan" should be -- Sultan Ahmad --.

Signed and Sealed this

Ninth Day of September, 2003

JAMES E. ROGAN
*Director of the United States Patent and Trademark Office*

SEQUENCE LISTING

```
(1) GENERAL INFORMATION:

   (iii) NUMBER OF SEQUENCES: 8


(2) INFORMATION FOR SEQ ID NO:1:

     (i) SEQUENCE CHARACTERISTICS:
          (A) LENGTH: 1714 base pairs
          (B) TYPE: nucleic acid
          (C) STRANDEDNESS: double
          (D) TOPOLOGY: linear

    (ii) MOLECULE TYPE: cDNA

   (iii) HYPOTHETICAL: NO

    (iv) ANTI-SENSE: NO

    (xi) SEQUENCE DESCRIPTION: SEQ ID NO:1:

CCGCGCGCAC ACCGCTCCCT CCACACCTCC AGGGGGAGTG AGCCACTCAA GTCTAAAGCA      60
```

-continued

```
GAGCGAGTCC CAGGACTTGA GCGCGGGAAG CGAATGGAGT CAGGGTCATT CGATTGCACC    120

TCTCTCGACT GCGGGCCGGA GCGGGGTACC ATCCTACACT CTGGGTGCTC CCTCCTCCTC    180

CCGTCCCCCG CGCACCCCTC CCCTGTCTCC TGGAGCTCGG CAGTCTCGCT GGGGCGCTGC    240

AGCGAGGGAG CAGCGTGCTC ACCAAGGACC CGGACAGCTG CGGGAGCGGC GTCCACTTTG    300

GTGATACCAT GAATGGCTCC GGCAGCCAGG GCGCGGAGAA CACGAGCCAG GAAGGCAGTA    360

GCGGCGGCTG GCAGCCTGAG GCGGTCCTTG TACCCCTATT TTTCGCGCTC ATCTTCCTCG    420

TGGGCACCGT GGGCAACGCG CTGGTGCTGG CGGTGCTGCT GCGCGGCGGC CAGGCGGTCA    480

GCACCACCAA CCTGTTCATC CTCAACCTGG GCGTGGCCGA CCTGTGTTTC ATCCTGTGCT    540

GCGTGCCTTT CCAGGCCACC ATCTACACCC TGGACGACTG GGTGTTCGGC TCGCTGCTCT    600

GCAAGGCTGT TCATTTCCTC ATCTTTCTCA CTATGCACGC CAGCAGCTTC ACGCTGGCCG    660

CCGTCTCCCT GGACAGGTAT CTGGCCATCC GCTACCCGCT GCACTCCCGA GAGTTGCGCA    720

CACCTCGAAA CGCGCTGGCC GCCATCGGGC TCATCTGGGG GCTAGCACTG CTCTTCTCCG    780

GGCCCTACCT GAGCTACTAC CGTCAGTCGC AGCTGGCCAA CCTGACAGTA TGCCACCCAG    840

CATGGAGCGC ACCTCGACGT CGAGCCATGG ACCTCTGCAC CTTCGTCTTT AGCTACCTGC    900

TGCCAGTGCT AGTCCTCAGT CTGACCTATG CGCGTACCCT GCGCTACCTC TGGCGCACAG    960

TCGACCCGGT GACTGCAGGC TCAGGTTCCC AGCGCGCCAA ACGCAAGGTG ACACGGATGA   1020

TCATCATCGT GGCGGTGCTT TTCTGCCTCT GTTGGATGCC CCACCACGCG CTTATCCTCT   1080

GCGTGTGGTT TGGTCGCTTC CCGCTCACGC GTGCCACTTA CGCGTTGCGC ATCCTTTCAC   1140

ACCTAGTTTC CTATGCCAAC TCCTGTGTCA ACCCCATCGT TTACGCTCTG GTCTCCAAGC   1200

ATTTCCGTAA AGGTTTCCGC AAAATCTGCG CGGGCCTGCT GCGCCCTGCC CCGAGGCGAG   1260

CTTCGGGCCG AGTGAGCATC CTGGCGCCTG GGAACCATAG TGGCAGCATG CTGGAACAGG   1320

AATCCACAGA CCTGACACAG GTGAGCGAGG CAGCCGGGCC CCTTGTCCCA CCACCCGCAC   1380

TTCCCAACTG CACAGCCTCG AGTAGAACCC TGGATCCGGC TTGTTAAAGG ACCAAAGGGC   1440

ATCTAACAGC TTCTAGACAG TGTGGCCCGA GGATCCCTGG GGGTTATGCT TGAACGTTAC   1500

AGGGTTGAGG CTAAAGACTG AGGATTGATT GTAGGGAACC TCCAGTTATT AAACGGTGCG   1560

GATTGCTAGA GGGTGGCATA GTCCTTCAAT CCTGGCACCC GAAAAGCAGA TGCAGGAGCA   1620

GGAGCAGGAG CAAAGCCAGC CATGGAGTTT GAGGCCTGCT TGAACTACCT GAGATCCAAT   1680

AATAAAACAT TTCATATGCT CTCGTGCCGA ATTC                                1714
```

(2) INFORMATION FOR SEQ ID NO:2:

(i) SEQUENCE CHARACTERISTICS:
- (A) LENGTH: 372 amino acids
- (B) TYPE: amino acid
- (C) STRANDEDNESS: Not Relevant
- (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:2:

```
Met Asn Gly Ser Gly Ser Gln Gly Ala Glu Asn Thr Ser Gln Glu Gly
1               5                   10                  15

Ser Ser Gly Gly Trp Gln Pro Glu Ala Val Leu Val Pro Leu Phe Phe
            20                  25                  30
```

-continued

```
Ala Leu Ile Phe Leu Val Gly Thr Val Gly Asn Ala Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
    370
```

(2) INFORMATION FOR SEQ ID NO:3:

(i) SEQUENCE CHARACTERISTICS:
(A) LENGTH: 1219 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

```
GGGTCAGCGG CACCATGAAC GTCTCGGGCT GCCCAGGGGC CGGGAACGCG AGCCAGGCGG     60
GCGGCGGGGG AGGCTGGCAC CCCGAGGCGG TCATCGTGCC CCTGCTCTTC GCGCTCATCT    120
TCCTCGTGGG CACCGTGGGC AACACGCTGG TGCTGGCGGT GCTGCTGCGC GGCGGCCAGG    180
CGGTCAGCAC TACCAACCTG TTCATCCTTA ACCTGGGCGT GGCCGACCTG TGTTTCATCC    240
TGTGCTGCGT GCCCTTCCAG GCCACCATCT ACACCCTGGA CGGCTGGGTG TTCGGCTCGC    300
TGCTGTGCAA GGCGGTGCAC TTCCTCATCT TCCTCACCAT GCACGCCAGC AGCTTCACGC    360
TGGCCGCCGT CTCCCTGGAC AGGTATTTGG CCATCCGCTA CCCGCTGCAC TCCCGCGAGC    420
TGCGCACGCC TCGAAACGCG CTGGCAGCCA TCGGGCTCAT CTGGGGGCTG TCGCTGCTCT    480
TCTCCGGGCC CTACCTGAGC TACTACCGCC AGTCGCAGCT GGCCAACCTG ACCGTGTGCC    540
ATCCCGCGTG GAGCGCCCCT CGCCGCCGCG CCATGGACAT CTGCACCTTC GTCTTCAGCT    600
ACCTGCTTCC TGTGCTGGTT CTCGGCCTGA CCTACGCGCG CACCTTGCGC TACCTCTGGC    660
GCGCCGTCGA CCCGGTGGCC GCGGGCTCGG GTGCCCGGCG CGCCAAGCGC AAGGTGACAC    720
GCATGATCCT CATCGTGGCC GCGCTCTTCT GCCTCTGCTG GATGCCCCAC CACGCGCTCA    780
TCCTCTGCGT GTGGTTCGGC CAGTTCCCGC TCACGCGCGC CACTTATGCG CTTCGCATCC    840
TCTCGCACCT GGTCTCCTAC GCCAACTCCT GCGTCAACCC CATCGTTTAC GCGCTGGTCT    900
CCAAGCACTT CCGCAAAGGC TTCCGCACGA TCTGCGCGGG CCTGCTGGGC CGTGCCCCAG    960
GCCGAGCCTC GGGCCGTGTG TGCGCTGCCG CGCGGGGCAC CCACAGTGGC AGCGTGTTGG   1020
AGCGCGAGTC CAGCGACCTG TTGCACATGA GCGAGGCGGC GGGGGCCCTT CGTCCCTGCC   1080
CCGGCGCTTC CCAGCCATGC ATCCTCGAGC CCTGTCCTGG CCCGTCCTGG CAGGGCCCAA   1140
AGGCAGGGCA GACAGGCATT CCTGACGGTT GATGTGGCCT TGAAAGGCAC TTAGCGGGCG   1200
CCTGGGATGT ACAGAGTTG                                                1219
```

(2) INFORMATION FOR SEQ ID NO:4:

(i) SEQUENCE CHARACTERISTICS:
(A) LENGTH: 385 amino acids
(B) TYPE: amino acid
(C) STRANDEDNESS: Not Relevant
(D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:4:

```
Met Asn Val Ser Gly Cys Pro Gly Ala Gly Asn Ala Ser Gln Ala Gly
1               5                   10                  15

Gly Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80
```

-continued

```
Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Ile Leu Glu Pro Cys Pro
        355                 360                 365

Gly Pro Ser Trp Gln Gly Pro Lys Ala Gly Gln Thr Gly Ile Pro Asp
    370                 375                 380

Gly
385
```

(2) INFORMATION FOR SEQ ID NO:5:

(i) SEQUENCE CHARACTERISTICS:
(A) LENGTH: 345 amino acids
(B) TYPE: amino acid
(C) STRANDEDNESS: Not Relevant
(D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:5:

```
Met Glu Leu Ala Pro Val Asn Leu Ser Glu Gly Asn Gly Ser Asp Pro
1               5                   10                  15
```

-continued

```
Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220

Leu His Lys Lys Leu Lys Asn Met Ser Lys Lys Ser Glu Ala Ser Lys
225                 230                 235                 240

Lys Lys Thr Ala Gln Thr Val Leu Val Val Val Val Val Phe Gly Ile
                245                 250                 255

Ser Trp Leu Pro His His Val Ile His Leu Trp Ala Glu Phe Gly Ala
            260                 265                 270

Phe Pro Leu Thr Pro Ala Ser Phe Phe Phe Arg Ile Thr Ala His Cys
        275                 280                 285

Leu Ala Tyr Ser Asn Ser Ser Val Asn Pro Ile Ile Tyr Ala Phe Leu
    290                 295                 300

Ser Glu Asn Phe Arg Lys Ala Tyr Lys Gln Val Phe Lys Cys Arg Val
305                 310                 315                 320

Asn Glu Ser Pro His Gly Asp Ala Lys Glu Lys Asn Arg Ile Asp Thr
                325                 330                 335

Pro Pro Ser Thr Asn Cys Thr His Val
            340                 345
```

(2) INFORMATION FOR SEQ ID NO:6:

(i) SEQUENCE CHARACTERISTICS:
(A) LENGTH: 349 amino acids
(B) TYPE: amino acid
(C) STRANDEDNESS: Not Relevant
(D) TOPOLOGY: Not Relevant (ii) MOLECULE TYPE: protein (iii) HYPOTHETICAL: NO (iv) ANTI-SENSE: NO -continued (xi) SEQUENCE DESCRIPTION: SEQ ID NO:6:

```
Met Glu Leu Ala Val Gly Asn Leu Ser Glu Gly Asn Ala Ser Cys Pro
1               5                   10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
        35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
                165                 170                 175

Phe His Pro Arg Ala Ser Asn Gln Thr Phe Cys Trp Glu Gln Trp Pro
            180                 185                 190

Asp Pro Arg His Lys Lys Ala Tyr Val Val Cys Thr Phe Val Phe Gly
        195                 200                 205

Tyr Leu Leu Pro Leu Leu Leu Ile Cys Phe Cys Tyr Ala Lys Val Leu
    210                 215                 220

Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                245                 250                 255

Gly Ile Ser Trp Leu Pro His His Ile Ile His Leu Trp Ala Glu Phe
            260                 265                 270

Gly Val Phe Pro Leu Thr Pro Ala Ser Phe Leu Phe Arg Ile Thr Ala
        275                 280                 285

His Cys Leu Ala Tyr Ser Asn Ser Ser Val Asn Pro Ile Ile Tyr Ala
    290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
            340                 345
```

(2) INFORMATION FOR SEQ ID NO:7:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “PCR primer”

-continued

```
   (iii) HYPOTHETICAL: NO

    (iv) ANTI-SENSE: NO

    (ix) FEATURE:
          (A) NAME/KEY: modified_base
          (B) LOCATION: group(25, 28, 31)
          (D) OTHER INFORMATION: /mod_base= i

    (xi) SEQUENCE DESCRIPTION: SEQ ID NO:7:

GGCCGTCGAC TTCATCGTCW MYCTNKCNYT NGCNGAC                    37


(2) INFORMATION FOR SEQ ID NO:8:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "PCR primer"

   (iii) HYPOTHETICAL: NO

    (iv) ANTI-SENSE: NO

    (ix) FEATURE:
          (A) NAME/KEY: modified_base
          (B) LOCATION: group(10, 13, 16)
          (D) OTHER INFORMATION: /mod_base= i

    (xi) SEQUENCE DESCRIPTION: SEQ ID NO:8:

RHWRCARTAN ATNATNGGRT T                                     21
```